(12) United States Patent
Toth

(10) Patent No.: US 7,280,635 B2
(45) Date of Patent: Oct. 9, 2007

(54) PROCESSES AND APPARATUS FOR MANAGING LOW KVP SELECTION AND DOSE REDUCTION AND PROVIDING INCREASED CONTRAST ENHANCEMENT IN NON-DESTRUCTIVE IMAGING

(76) Inventor: Thomas Louis Toth, 3000 N. Grandview Blvd. W1140, Waukesha, WI (US) 53188

( * ) Notice: Subject to any disclaimer, the term of this patent is extended or adjusted under 35 U.S.C. 154(b) by 203 days.

(21) Appl. No.: 11/291,882

(22) Filed: Dec. 1, 2005

(65) Prior Publication Data

US 2007/0140428 A1 Jun. 21, 2007

(51) Int. Cl.
*H05G 1/44* (2006.01)

(52) U.S. Cl. .............. 378/108; 378/98.7; 378/112; 378/117; 378/207

(58) Field of Classification Search ......... 378/98–98.8, 378/108–118, 207, 210, 901; 250/358.1, 250/359.1, 360.1
See application file for complete search history.

(56) References Cited

U.S. PATENT DOCUMENTS

| 5,594,767 | A | 1/1997 | Hsieh |
| 5,761,333 | A | 6/1998 | Hsieh et al. |
| 6,222,907 | B1 * | 4/2001 | Gordon et al. .............. 378/116 |
| 6,826,252 | B2 * | 11/2004 | Heismann .................... 378/16 |

\* cited by examiner

*Primary Examiner*—Jurie Yun
(74) *Attorney, Agent, or Firm*—Peter Vogel; Fritz Fliegel (57) ABSTRACT

Systems, processes and apparatus are described through which non-destructive imaging is achieved, with equivalent or increased contrast, in comparison to conventional approaches, and that facilitate reduced dosage of X-rays delivered to the object or patient being imaged.

20 Claims, 7 Drawing Sheets

PROCESSES AND APPARATUS FOR MANAGING LOW KVP SELECTION AND DOSE REDUCTION AND PROVIDING INCREASED CONTRAST ENHANCEMENT IN NON-DESTRUCTIVE IMAGING

FIELD OF THE DISCLOSURE

This disclosure relates generally to nondestructive evaluation, including medical diagnosis, and more particularly to diagnosis of presenting conditions based on internal images of a test subject, such as a living patient.

BACKGROUND

Many medical diagnoses rely on non-invasive diagnostic tools to provide information, usually in the form of images, descriptive of status of internal portions or organs of a patient. These tools include thermal imaging (e.g., mammography), ultrasonic probes, magnetic resonance imaging techniques, positron emission tomography, computed tomography (CT), single photon emission-computed tomography (SPECT), optical imaging and/or X-ray based techniques. In some instances, imaging aids, such as contrast-enhancing agents, are introduced into the subject or patient to aid in increasing available data content from the non-destructive or non-invasive imaging technique or techniques being employed.

Each of these tools presents advantages in particularized situations, has technological limitations, may require set-up and analysis time, can include risks and also has associated costs. As a result, a cost-benefit analysis that also reflects the urgency or lack thereof with respect to a particular diagnostic trajectory often favors usage of X-ray based measurement techniques.

However, exposure to X-rays can result in some risk to the test subject or patient. For at least this reason, the dosage of X-rays incident on the patient, organ or object being evaluated/imaged, is often carefully chosen and controlled, for example, by selecting an area to be exposed, current to the X-ray tube, peak voltage applied to the X-ray tube (kVp) and exposure time, to provide successful imaging, based on the task and the test subject or patient's parameters, with least health risk to the patient or radiation exposure to the object being imaged. The Food and Drug Administration has recently identified X-rays as potentially having carcinogenic effects, adding impetus to the desire to reduce overall exposure while still providing imaging characteristics capable of enabling rapid, effective and accurate diagnostic aids.

Several factors influence the Image Quality or IQ resulting from an X-ray procedure. Statistical photon noise resulting from characteristics of the X-ray source and the X-ray generation conditions tends to dominate other noise sources in formation of an X-ray image. Contrast between various image portions, and contrast enhancement techniques, are also important considerations in providing diagnostic images, and these issues require increasingly sophisticated treatment as dose and/or photon energy are decreased.

For the reasons stated above, and for other reasons discussed below, which will become apparent to those skilled in the art upon reading and understanding the present disclosure, there are needs in the art to provide test data in support of reliable diagnoses of medical conditions and diseases from medical anatomical images, providing contrast equal to or exceeding that of conventional approaches, yet using reduced exposure parameters when feasible, consistent with the imaging task.

SUMMARY

The above-mentioned shortcomings, disadvantages and problems are addressed herein, which will be understood by reading and studying the following disclosure.

In one aspect, a process for managing dose and contrast in a non-destructive imaging system is disclosed. The process includes acts of (i) accepting user input data indicative of image quality goals and a drive parameter setting strategy for an illumination source to be employed in the non-destructive imaging of a test subject and (ii) determining when the non-destructive imaging system is capable of achieving the image quality goals using a particular drive parameter setting selected from among a group of achievable drive parameter settings. A first of the group of drive parameter settings corresponds to a lowest drive parameter setting for the non-destructive imaging system. The first drive parameter setting is initially chosen as the particular drive parameter setting. The process also includes acts of (iii) proceeding with a non-destructive imaging procedure when determining does not indicate that the non-destructive imaging system is incapable of achieving the image quality goals at the particular drive parameter setting and (iv) replacing the particular drive parameter setting with an incrementally increased particular drive parameter setting when determining indicates that the non-destructive imaging system is capable of achieving the image quality goals. The process also includes (v) iterating determining, proceeding or increasing, and iterating, until either proceeding is achieved or all available drive parameter settings have been tested, and, when all drive parameter settings have been tested and determining continues to indicate incapability, generating a message to an operator of the system.

In another aspect, a non-destructive imaging system includes an illumination source. The illumination source is configured to internally illuminate a test subject in generating an image of at least an internal portion of the test subject. The imaging system also includes a controllable driver coupled to the illumination source. The controllable driver includes capability for multiple drive parameter settings for the illumination source. The imaging system further includes a user interface capable of accepting user input data indicative of image quality goals and a user choice of at least one of a plurality of drive parameter selection strategies for the illumination source. The imaging system also further includes a control module configured to (i) initially select a lowest of the multiple drive parameter settings as a selected setting, (ii) model the selected setting in the context of the user choice of drive parameter selection strategies to determine when the selected setting is capable of achieving the image quality goals, (iii) replace the selected setting with an incrementally increased value for the selected setting when the control module test indicates that the image quality goals cannot be met at the selected setting, and (vi) proceeding with imaging the test subject when the control module test indicates that the image quality goals can be met at the selected setting.

In a yet another aspect, an article of manufacture embodies computer code thereon that includes computer-readable instructions, which, when executed by one or more processors, causes the one or more processors to perform acts of (i) accepting user input data indicative of image quality goals and a drive parameter setting strategy for a high power X-ray source to be employed in non-destructive imaging of a test subject using an X-ray system, and (ii) determining when the X-ray system is capable of achieving the image quality goals using a particular drive parameter setting selected from among a group of achievable drive parameter settings. A first of the group of drive parameter settings corresponds to a lowest drive parameter setting for the high power X-ray source, and the first drive parameter setting is initially chosen as the particular drive parameter setting. The computer readable instructions are also configured to cause the one or more processors to perform acts of (iii) proceeding with an X-ray procedure when determining does not indicate that the X-ray system is incapable of achieving the image quality goals at the particular drive parameter setting, (iv) replacing the particular drive parameter setting with an incrementally increased particular drive parameter setting when determining indicates that the X-ray system is capable of achieving the image quality goals and (v) iterating determining, proceeding or increasing, and iterating, until either proceeding is achieved or all available drive parameter settings have been tested, and, when all drive parameter settings have been tested and determining continues to indicate incapability, generating a status message.

Systems, clients, servers, processes, and computer-readable media of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which are shown, by way of illustration, specific embodiments which may be practiced. These embodiments are described in sufficient detail to enable those skilled in the art to practice the embodiments, and it is to be understood that other embodiments may be utilized, and that logical, mechanical, electrical and other changes may be made without departing from the scope of the embodiments. As used herein, the term "illumination" refers to exposure to photons, electromagnetic radiation or other wave phenomena, which do not necessarily correspond to light that is visible to a human eye. Ranges of parameter values described herein are understood to include all subranges falling therewithin. The following detailed description is, therefore, not to be taken in a limiting sense.

The detailed description is divided into five sections. In the first section, a system level overview is described. In the second section, modeling schemes for contrast mapping and/or selective enhancement in at least portions of one or more images are described. In the third section, embodiments of processes are described. In the fourth section, hardware and an operating environment in conjunction with which embodiments may be practiced are described. In the fifth section, a conclusion of the detailed description is provided. A technical effect of the systems and processes disclosed herein includes at least one of facilitating capability for reduced dose exposure of a subject being imaged to X-rays, imaging of internal portions of a test subject at reduced kVp, and maintaining diagnostically useful contrast and contrast-to-noise parameters in non-destructive imaging.

I. System Overview

Figure 1:
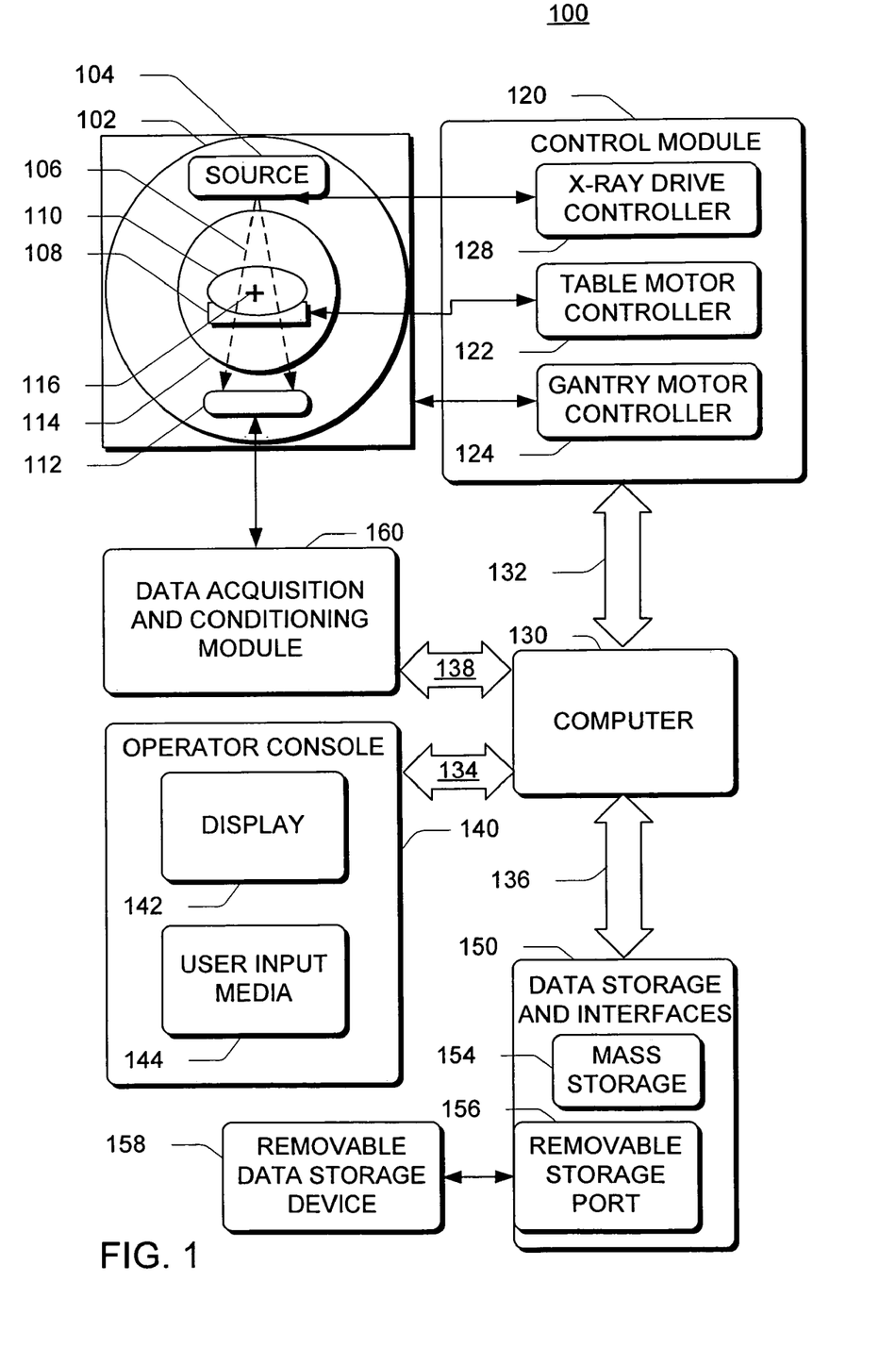
FIG. 1 is a simplified block diagram of an overview of a system configured to improve X-ray imaging operations.

FIG. 1 is a simplified diagram of an overview of a system 100 configured to improve X-ray imaging operations. In particular, the system 100 is configured to maintain or increase contrast in non-destructive imaging systems based on X-radiation, while reducing the radiation dose delivered to the object or patient being imaged, compared to conventional X-ray imaging systems and processes. The system 100 includes a gantry 102 or other support for an illumination source 104, such as an X-ray illumination source, capable of providing illumination 106, such as X-rays and/or other non-destructive internal imaging illumination, a test subject support 108, configured to support and/or cause controlled motion of a test subject 110, such as a living human or animal patient, or other test subject suitable for non-destructive imaging, and a detector 112 postured opposed to the illumination source 104. The detector 112 may be conventional film or a scintillator coupled to an array of photodiodes, such as a conventional two-dimensional array of photodiodes and suitable control transistors formed using polycrystalline silicon, or any other type of conventional detector suitable for use with X-rays.

In some modes of operation, such as CT, the gantry 102 and test subject support or table 108 cooperatively engage to move the test subject 110 longitudinally, that is, along an axis extending into and out of the plane of FIG. 1 and within an opening 114. In some modes of operation, the gantry 102 rotates the X-ray source 104 and detector 112 about an axis 116 to provide a helical series of scans of the test subject 110, where a pitch of the helices is defined as a ratio of a longitudinal distance traveled by the table 108 during a complete revolution of the gantry 102, compared to a length of the detector 112 along the axis of linear motion.

For example, when a longitudinal distance traveled by the table 108 during a single rotation of the gantry 102 is 40 millimeters and the length of the detector 112 along the axis of motion is also 40 millimeters, the pitch is one, with increased motion of the table 108 relative to length of the detector 112 during a revolution of the gantry 102 resulting in higher pitch. In general, lower pitch results in increased X-ray dose delivered to the test subject 110. The motion of the test subject support 108 and/or gantry 102 may be varied in conformance with a desired set of exposure parameters and/or image quality indices, as is explained below in more detail with reference to Section II et seq.

The system 100 also includes a control module 120, which may include a test subject support or table control module 122 configured to move the test subject support 108 and thus the test subject 110 relative to the X-ray source 104 and/or detector 112, and may include a gantry motor controller 124 or other controller for positioning the X-ray illumination source 104 relative to the test subject 110 and/or the detector 112. For example, in some types of imaging tasks, the X-ray illumination source 104 is rotated in a circular pattern within a fixed plane at a fixed height above the region of the test subject 110 being studied, and the X-ray source 104 provides a cone-shaped locus of X-rays 106, over the region being imaged.

The controller 120 includes a drive parameter controller 128 configured to control electrical drive parameters delivered to the X-ray source 104. One or more computers 130 provide connections to the controller 120 via a bus 132 configured for receiving data descriptive of operating conditions and configurations and for supplying appropriate control signals, as will be described below in more detail with reference to Section II et seq. The computer 130 also includes a bus 134, a bus 136 and a bus 138. The bus 134 couples the computer 130 to an operator console 140.

The operator console 140 includes one or more displays 142 and a user input interface 144. The user input interface 144 may include a keyboard, a mouse or other tactile input device, capability for voice commands and/or other input devices. The one or more displays 142 provide information relative to operation of system 100, user-selectable options and images descriptive of the test subject 110, and may include a graphical user interface for facilitating user selection among various modes of operation and other system settings.

The system 100 also includes memory devices 150 forming a memory system, coupled via the bus 136 to the computer 130 through suitable interfaces. The memory devices 150 include mass data storage capabilities 154 and one or more removable data storage device ports 156. The one or more removable data storage device ports 156 are adapted to removably couple to portable data memories 158, which may include optical, magnetic and/or semiconductor memories and my have read and/or write capabilities, and which may be volatile or non-volatile devices or may include a combination of the preceding capabilities.

The system 100 further includes a data acquisition and conditioning module 160 that has data inputs coupled to the detector 112 and that includes that is coupled by the bus 138 to the one or more computers 130. The data acquisition and conditioning module 160 includes analog to digital conversion circuitry for capturing data from the detector 112 and then converting those data from the detector 112 into digital form, to be supplied to the one or more computers 130 for ultimate display via at least one of the displays 142 and for potential storage in the mass storage device 154. The acquired image data may be conditioned, as described below with reference to Section II et seq., in either the data acquisition and conditioning module 160 or the one or more computers 130 or both.

II. Contrast Model Overview

The Hounsfield scale (named after Sir Godfrey Hounsfield, the seminal discloser of CT concepts) is a tool for mapping effective linear attenuation coefficients which comprise X-ray or CT images to a convenient standard numeric scale. Values on this scale are expressed in Hounsfield Units (HU) and are sometimes referred to as CT numbers. On the HU scale, the value of water in a CT image is zero and the value of air is −1000. The scale $HU_x$ is defined as:

$$HU_x = (\mu_x - \mu_w)(1000)\mu_w, \quad \text{(Eq. 1)}$$

where $\mu_x$ represents an effective linear attenuation coefficient for a pixel as determined by the image reconstruction process, $\mu_w$ represents an effective linear attenuation coefficient for water, and $HU_x$ represents the Hounsfield Unit value for pixel x. Eq. 1 does not have to be explicitly implemented as given, since HU mapping can be achieved by appropriate system scale factors, and offsets may applied during the image reconstruction process. These scale factors, when employed to provide a match to obtain the air and water HU scale values, are kVp-dependent, where kVp is understood to mean kilo volts peak, as applied to the X-ray source or tube 104.

In many imaging tasks, diagnostic utility of data from the detector 112 is improved by focusing on a portion of the relationship described by Eq. 1, and mapping that portion over a range of display values extending from low or no luminance to full luminance. This can be augmented via renormalization of the Hounsfield units to Hounsfield Normalized Units, as described below in more detail with reference to FIG. 2.

Figure 2:
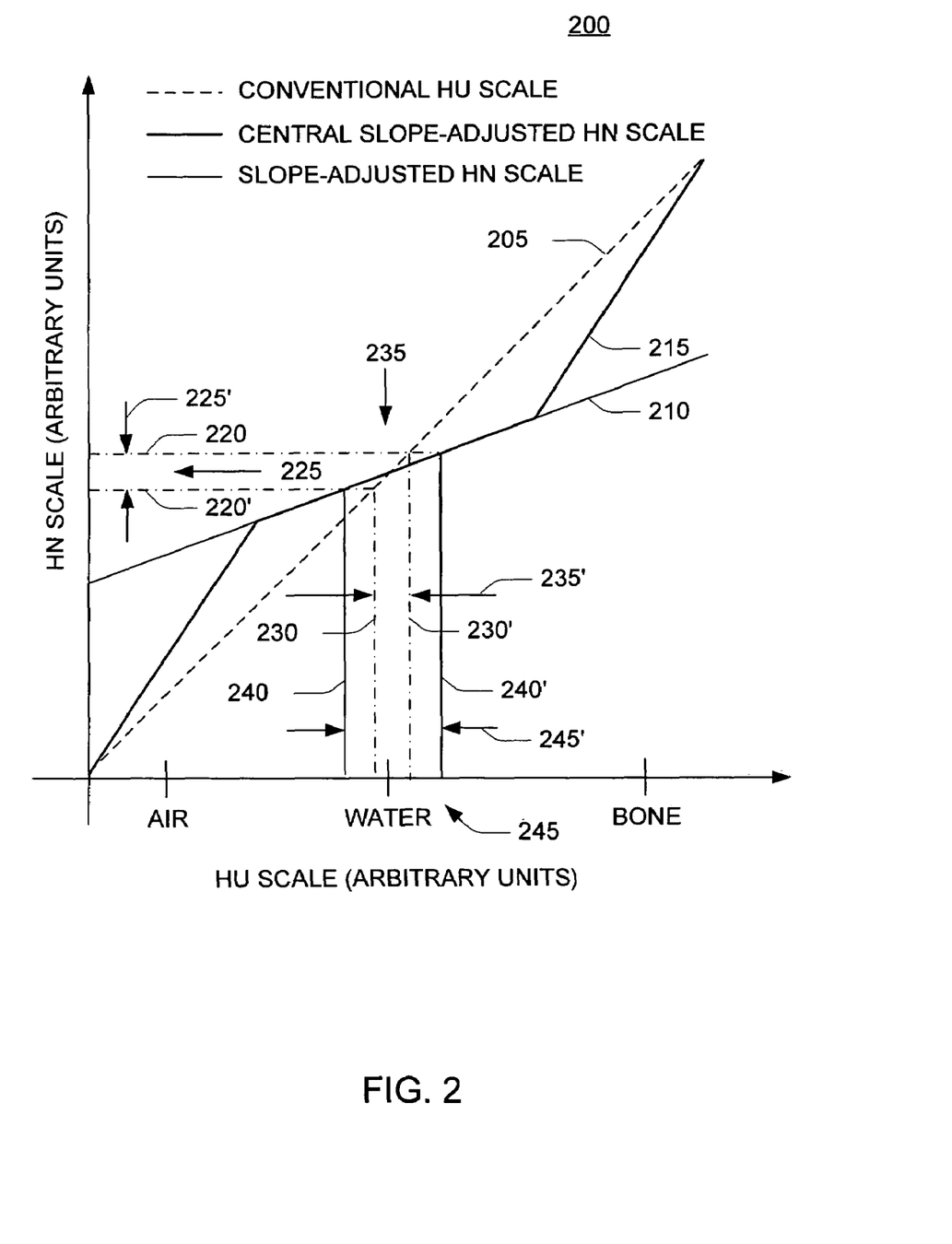
FIG. 2 depicts a graph illustrating exemplary relationships between Hounsfield Units (HU scale) and Hounsfield Normalized Units (HN scales).

FIG. 2 depicts a graph 200 illustrating exemplary relationships between Hounsfield Units (HU scale) and Hounsfield Normalized Units (HN scales). The graph 200 shows the unmodified relationship described above with respect to Eq. 1 as a dashed line 205, and illustrates modified relationships as solid trace 210, corresponding to a slope-adjusted Hounsfield Normalized scale, and heavy solid trace 215, corresponding to a central slope adjusted HN scale, which in this example is piecewise linear, although other mappings (e.g. curvilinear and the like) are possible and useful in the context of the present disclosure.

To visualize an image from data expressed in Hounsfield units, data display window and level values are selected to translate image pixel values from Hounsfield units to a brightness gray scale within the selected window and to render image pixel values outside of the selected window to either a compressed scale or to an extremal value. For example, to view soft tissue images, a level corresponding to one side of the selected window might be adjusted to a level of −50 HU, together with a window width of 200 HU, as indicated in FIG. 2 by dashed lines 220, 220' on the HN scale. For example, this could result in a display where all pixel values of −50 HU or less as shown as corresponding to one extremal value, such as being fully black, and all values of 150 HU or more being displayed at another extremal value, such as full brightness. Pixel image data values in between edges of the window, or −50 HU (represented by dashed line 220 ) and 150 HU (represented by dashed line 220'), in the window interval 225 or width, in this example, would be mapped to some appropriate shade of gray intermediate between the black and full brightness extremes. For visualizing high contrast objects, such as for viewing lung tissue against an air sac background, the window and level might be set to a level of −800 and a window width of 1500 (not illustrated in FIG. 2).

In this way, the radiologist can zoom in to visualize low contrast details, or zoom out to view a wider range of contrast values. Both the object contrast and the noise will appear more intense with smaller window width settings. Radiologists who do virtually all scanning at 120 kVp or 140 kV have become accustomed to an expected set of window and level settings for viewing images of various anatomic regions for various CT clinical procedures. Settings of 120 kVp and 140 kVp are used almost exclusively, because, until recently, x-ray tubes 104 with sufficient tube current loading were not available to produce images for typical test subjects or patients 110 with sufficiently low noise at lower kVp. Images with noise levels low enough to enable a confident diagnosis are among the most important image quality concerns to the radiologist.

When properly managed, the increased tissue contrast with lower kVp offers significant dose efficiency (reduction) advantages and therefore presents desirable options to the radiologists, compared to the conventional 120 kVp or 140 kVp settings in conventional clinical use. High power tubes with 100 kW capability such LightSpeed® Pro X-ray tubes, available from the General Electric Company, of Waukesha Wis., can permit procedures to be done at lower kVp settings, together with acceptable image noise, than conventional X-ray tubes 104 are capable of. However, even with high power tubes 104, not all patients can be scanned using reduced kVp settings.

The use of lower kVp however, increases the HU difference between soft tissue (contrast) from width 235' to width 245' for example, as shown in FIG. 2. This increase would require the radiologist to increase the window width to obtain the same visual grey scale as at the higher kVp. FIG. 2 illustrates two ways in which the HU scale can be re-mapped to an HN scale which is displayed to an image to avoid re-adjustment of the window width. In one of these approaches, the HU value of water is maintained, while linearly adjusting the slope through that value, as represented by trace 210, with the first data window edges 220, 220' (horizontal dot-dash lines) of the data window 225 corresponding, respectively, to second data window edges represented by lines 230, 230' (dashed vertical lines) and a second data window 235 having a width 235' on the ordinate, and/or corresponding to third data window edges 240, 240' (solid vertical lines) and third data window 245 having an expanded width 245'.

In this case, the value of air would not be −1000 but might be a number of such as between about −900 and −750 at 100 and 80 kVp, respectively. This might be acceptable if the intercept for air or bone is not so important, for example, in imaging soft tissue structures. In another of these approaches, which may be piece-wise linear or a spline fit to such, as represented by trace 215, the HU mapping slope is reduced for the soft tissue region while still preserving the HU value of 0 for water and −1000 for air. For example, the HU values of a one or more of a predetermined set of criteria may be mapped to identical HN values, but the shape of the HN curve may be distorted in a window region that is postured relative to a portion of the HU and HN curves that is particularly relevant to the imaging task and/or conditions of a specific measurement type, or to a specific measurement type and considerations based on parameters relevant to the test subject 110 being imaged. Alternatively, one or more of the HU values for predetermined criteria may be preserved in mapping to HN values, with one or more other predetermined criteria HU values being mapped in a predetermined fashion to a revised HN value (e.g., the HU value for water may be unchanged in mapping HU values to HN values, but the HU value for air allowed to increase in deriving HN values. Exemplary predetermined criteria may include one or more of HU and HN values for water, air, hard bone and other characteristic features having well-known opacity.

Each of these approaches maps an HU tissue range that changes with kVp (width 235' to width 245' for example) to a more consistent range (width 225') to allow the radiologist to view the image data without changing the gray scale window when different kVps are used.

Some of the benefits of low kVp scans appear below in Table I (calculated by computer modeling and rounded off to the nearest one percent). Table I shows estimated percentages of contrast increase for several tissues types relative to water scanned at 140 kVp, for three lower kVp values, viz., 120 kVp, 100 kVp and 80 kVp, as well as for Iodine, which is one example of a conventional contrast enhancement agent employed in certain types of radiological imaging applications.

TABLE I

| | Voltage (kV) | | |
|---|---|---|---|
| | 120 | 100 | 80 |
| Iodine | 24 | 66. | 145 |
| Fat | 9 | 23 | 51 |
| Muscle | −3.81356 | −11 | −28 |
| Liver | 4 | 10 | 20 |
| Blood | 5 | 12 | 26 |

Percent Contrast Increase Relative To Water Scanned At 140 kVp For Three Other Voltages.

In particular, as shown in Table I, the HU value for Iodine (used as a common contrast enhancement agent) increases by 24%, 66% and 145%, as the kVp value is lowered from 140 kVp to 80 kVp. Also, non-contrast-enhanced soft-tissue differentiation increases, as the kVp value is lowered. For example, the difference in HU values between fat and muscle is 12%, 33% and 77%, as the kVp value is decreased from 120 kVp to 100 kVp to 80 kVp, respectively. Other common non-contrast-enhanced human/animal tissue examples also show increases in HU separation with decreases in kVp. A conservative average over these kinds of tissues shows that soft tissue contrast increases by 0% to 10% and to 25%, as the kVp value is lowered to 120 kVp to 100 kVp to 80 kVp, respectively.

When the current level to the X-ray source 104 is increased to maintain the same image noise level, the dose delivered to the test subject 110 increases by 5% (at 120 kVp), 9% (at 100 kVp) and 24% (at 80 kVp), respectively, as compared to 140 kVp, thus providing the same visual image noise for the viewing windows as is expected by the radiologist using 140 kVp. In imaging for medical diagnosis purposes, the radiologist needs to clearly see the non-contrast-enhanced soft tissue in order to make a confident diagnosis, when a abnormality such, as a lesion is present, but without increasing the dose of X-rays delivered to the patient (unless such is needed for reasons other than contrast, e.g., due to the patient's weight).

The contrast improvement that are possible for images of soft tissue as kVp is decreased offer opportunity to provide diagnostically useful images by increasing the noise index by an amount that provides an equivalent dose of X-radiation (e.g., 5% and 10% contrast improvements for 100 kVp and 80 kVp, respectively) to the test subject 110, which is called the equivalent dose kVp (ED) selection strategy. The ED strategy increases the noise in the image over that to which the radiologist is accustomed, but still provides a soft tissue contrast to noise (CNR) advantage. That is, even though the image noise has increased, the contrast differences in HU values for soft tissue have increased by a greater amount. The CNR advantage with ED is reduced to 5% and 15% (100 and 80 kVp), compared to the average figures of 10% and 25% described above with reference to Table I.

Another low kVp selection strategy, the equivalent CNR selection strategy (ECNR), increases the noise index to match the soft tissue contrast improvement, providing a CNR equivalent to high kVp (10% and 25% at 100 and 80 kVp). The ECNR strategy increases image noise by the same factor as the soft tissue contrast increase, and results in a dose reductions of 10% and 30% at 100 and 80 kVp.

Either the ED or ECNR strategy results in substantially increased image noise, compared to what the radiologist is accustomed to viewing. As a result, the images will appear noisy if viewed at the same window level settings. This may be overcome by increasing the window width by the same factor as the noise increase, producing a similar visual appearance in the gray scale image as with the lower noise at the higher kVp settings. As a practical matter, this is not a useful solution, because images are prepared at different kVp values, depending on patient size and tube mA capabilities, and window level settings require kVp-dependent changes. As a result, the radiologist would have to constantly be attentive to thekVp used for the scan and would constantly be resetting viewing settings to different HU scale values.

Additionally, sometimes the HU value of an anatomic region in an image is measured and the results are compared to a threshold value as a factor to help determine the presence of disease. However, the expected anatomical HU threshold values change, depending on kVp, which may cause additional complications for the radiologist.

The noise increase issues noted with respect to the ED or ECNR strategies may be resolved by increasing the gray scale window by a factor equivalent to the noise increase. Also, a pseudo-HU image, using a Hounsfield Normalized scale (HN), may be created by remapping the HU values within the soft tissue region inversely to the soft tissue contrast increase. This HN strategy maintains similar soft tissue HU values for low kVp as for high kVp, and also reduces the visual image noise, avoiding need for the radiologist to adjust viewing windows, and better maintains the expected HU readings for soft tissue components.

A third low kVp selection strategy is one that may be called Aggressive Dose Reduction (ADR). Tissue images that are contrast-enhanced with iodine will increase in contrast very dramatically (65% and 145% at 100 kVp and 80 kVp). There may be some clinical situations, such as CT angiograms, for example, where the loss of soft tissue CNR may not be clinically significant. In this case, an aggressive dose reduction may be possible. For example, being highly conservative and employing only half the available Iodine contrast increase toward dose reduction, the radiologist may be able to increase the noise index by 20% and 50% (or possibly more) at 100 kVp and 80 kVp. This may result in dose reductions of 25% and 50%, at 100 kVp and 80 kVp, respectively. Process embodiments of these strategies for providing diagnostically-useful images together with reduction of the dose of X-radiation delivered to the test subject 110 are described below in more detail with reference to FIGS. 3 through 6.

III. Process Embodiments

In the previous section, an overview of modeling and mapping techniques for improving contrast in medical imaging was described. In this section, the models of that section are used in describing the operation of a series of embodiments, with the particular processes of such embodiments being described by reference to relevant flowcharts. Describing the processes by reference to one or more flowcharts enables one skilled in the art to develop programs, firmware, or hardware, including such instructions to effectuate the processes through one or more processors responsive to computer-readable instructions embodied on computer-readable media. This is often accomplished using suitable computers, including one or more processors, by executing the instructions embodied computer-readable media, or as modulated signals embodied in a carrier wave. Similarly, the processes performed by server computer programs, firmware, or hardware also are represented by computer-executable instructions. The processes of the present disclosure are performed by one or more program modules executing on, or performed by firmware or hardware that is a part of, a computer, such as the computer 130 in FIG. 1.

In some embodiments, processes disclosed herein are implemented as a computer data signal embodied in a carrier wave, that represents a sequence of instructions which, when executed by one or more processors, such as a processor contained in or associated with the computer 130 in FIG. 1, causes the respective process to occur. In other embodiments, the processes disclosed herein are implemented as a computer-accessible medium having executable instructions capable of directing a processor, such as a processor contained in or associated with the computer 130 in FIG. 1, to perform the respective process. In varying embodiments, the medium is a magnetic medium, an electronic medium, or an electromagnetic/optical medium.

More specifically, in a computer-readable program embodiment, programs can be structured in an object-orientation using an object-oriented language such as Java, Smalltalk or C++, and the programs can be structured in a procedural-orientation using a procedural language such as COBOL or C. Software components may communicate in any of a number of ways that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 130 in FIG. 1, or on multiple computers.

Figure 3:
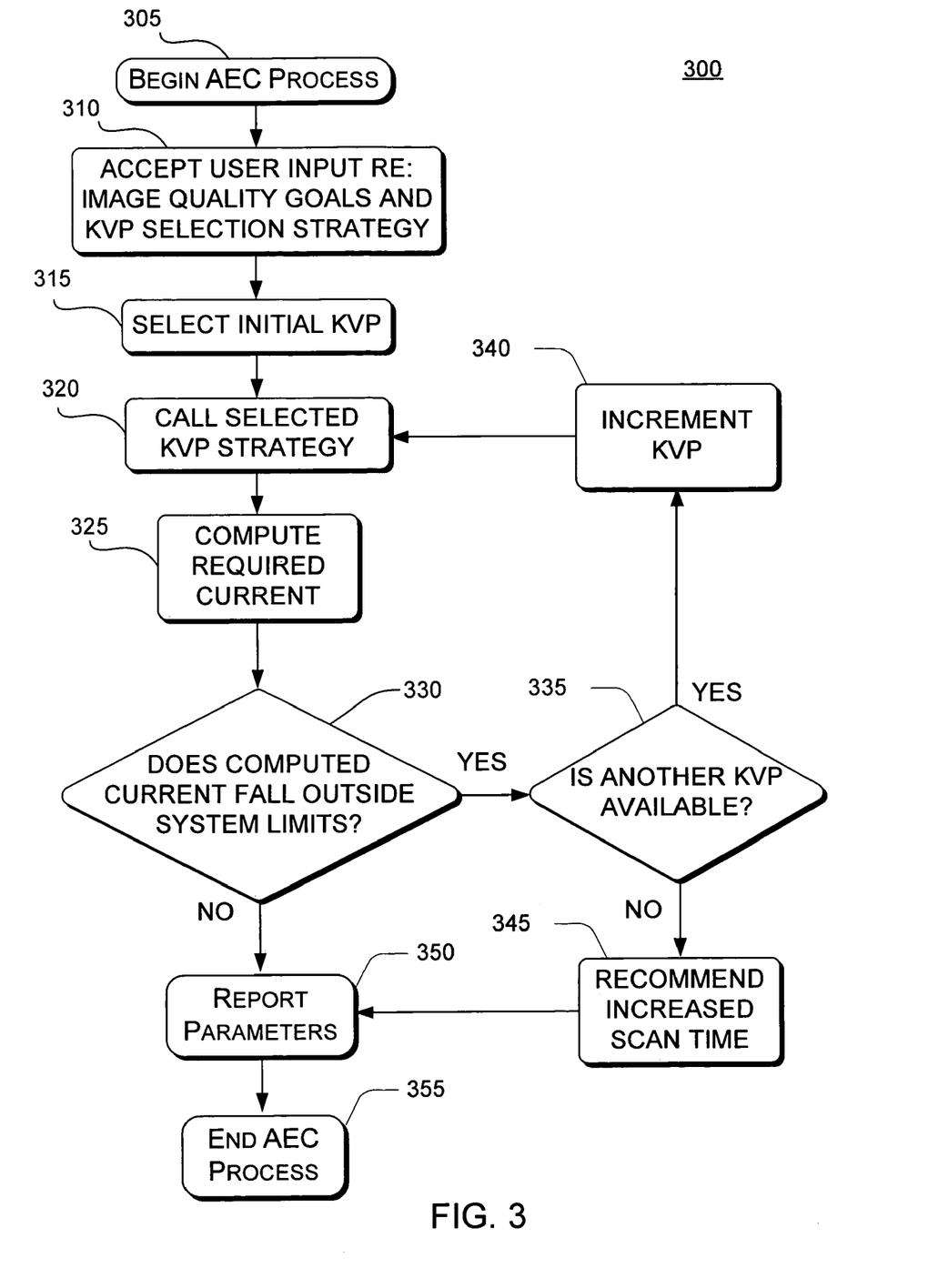
FIG. 3 shows a flowchart describing an Automatic Exposure Control (AEC) process that finds utility in the system of FIG. 1.

FIG. 3 shows a flowchart 300 describing an Automatic Exposure Control (AEC) process that finds utility in the system of FIG. 1. The AEC process is used for calculating patient attenuation in order to set the X-ray tube or source current level in mA for a given kVp setting to achieve a given image quality goal. The process 300 begins in a block 305. Control then passes to a block 310.

In the block 310, the image quality goal can be specified by the radiologist in terms of a Noise Index, Image Noise, a reference image, and/or an effective X-ray tube current (measured in milli-Amperes) for a nominal patient or test subject. The radiologist also selects among a variety of kVp selection strategies, as described below with reference to FIG. 3 et seq. in the block 310. Control then passes to a block 315.

In the block 315, an initial test kVp setting is selected from a group of kVp settings that the system 100 is capable of. The initial selection is generally the lowest of the kVp settings that the system 100 offers. Control then passes to a block 320.

In the block 320, the process 300 calls a subroutine corresponding to the exposure strategy selected by the radiologist. For example, the process 300 may call one of the subroutines described below with reference to FIGS. 4 through 6. Control passes to a block 325 after the selected subroutine is executed.

In the block 325, the process 300 computes the current required to drive the X-ray source 104 at the selectedkVp setting that is consistent with image quality goals selected in the, block 310 and particular conditions relative to the selected test subject 110. The current also is computed in conformance with the exposure strategy that was selected with the radiologist in the block 310.

In a query task 330, the process 300 determines when the current required at the selected kVp and strategy exceeds the capabilities of the system 100. When the query task 330 determines that the current required for the selected options exceeds capabilities of the system 100, control passes to a query task 335. In the query task 335, the process 300 determines when a higher kVp setting is available.

When the query task 335 determines that another kVp setting is available, control passes to a block 340. In the block 340, the selected kVp is altered, for example, may be increased. In one embodiment, kVp may be automatically variable in predetermined increments, such as 20 kilo volts or one kilo volt. In one embodiment, kVp may be automatically variable in fine increment or continuously variable manner. In one embodiment, the radiologist may vary a selected kVp value in increments such as 10 or 20 kilo volt steps. The process 300 then iterates from the block 320 forward until either a suitable kVp and current setting is determined, or it is determined that the process 300 is not able to match the criteria to capabilities of the system 100.

When the query task 335 determines that no greater kVp is available to the system 100, the process 300 optionally recommends, via the operator console 140, options such as increased scan time, in a block 345.

After the process 300 suggests options such as alternative exposure strategies, or increased scan time etc. in the block 345, or when the query task 330 determines that the current required does not exceed capabilities of the system 100, control passes to a block 350.

In the block 350, the system 100 displays results of the process 300, such as via the display 142 of FIG. 1. The process 300 may indicate, for example, that the system 100 cannot achieve the selected image quality goals within the range of other parameters, or the process 300 may generate a status message, e.g., to report all scan parameter values automatically recommended by the process 300 to the operator for confirmation prior to scanning (such as kVp, tube current, speed, pitch, etc).

In one embodiment, the process 300 automatically tests and reports various scan speeds, pitches, etc. over a suitable range appropriate to image quality goals for at least some kVp values tested. The process 300 then ends in a block 355, and the imaging task then proceeds.

As a result, the AEC process 300 is able to determine when a patient is too large for the presently-selected parameters to be likely to provide diagnostically useful images relative to the imaging task at hand and thus could require a current setting beyond the capability of the system 100 at low kVp. In turn, this allows the radiologist opportunity to reduce a dose that is delivered to the test subject 110 while preserving diagnostic utility of resultant images.

The AEC process 300 allows systems 100 to eliminate one obstacle to employing reduced kVp, as compared to conventional X-ray imaging systems, by rejecting kVp settings that are too low to permit the IQ goals specified in the block 310 to be achieved. This prevents the technologist from using a kVp setting that would produce an image lacking in appropriate diagnostic value and which therefore could de-motivate the radiologist from using reduced kVp scans, in comparison to conventional exposure setting processes. To use reduced kVp settings, the system 100 may automatically start with the lowest available kVp, and model and/or test to determine when the system 100 can achieve the desired image noise with the particular test subject 110. When the process 300 determines that the system 100 cannot achieve the desired image quality goals, the system 100 sequentially models incrementally higher kVp settings until the system 100 determines a lowest available kVp setting that can achieve the IQ goal. The process 300 also includes capability for determining when using slower scan speeds or lower helical pitches permit the system 100 to meet the IQ goal at a given kVp setting, as well as facilitating determination of when the IQ goal can not be achieved at default scan speed and/or pitch settings.

Figure 4:
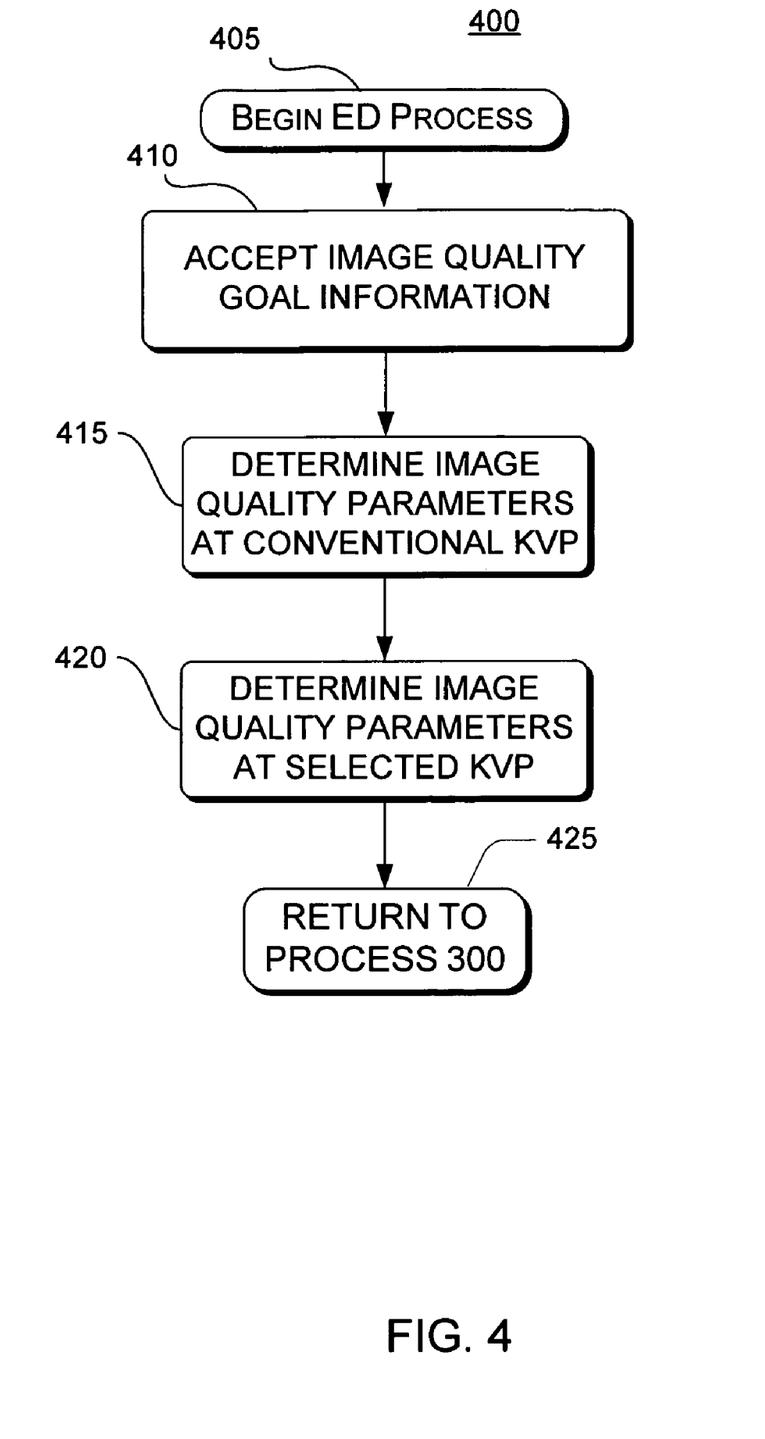
FIG. 4 shows a flowchart describing an Equivalent Dose (ED) exposure process that finds utility in the system of FIG. 1.

FIG. 4 shows a flowchart describing an Equivalent Dose (ED) exposure process 400 that finds utility in the system 100 of FIG. 1. The radiologist has indicated a preferred option for selecting among several different exposure options in the block 310 of FIG. 3. The process 400 begins in a block 405. Control then passes to a block 410.

In the block 410, desired image quality goal information is determined. For example, a radiologist may specify a desired image quality goal in terms of acceptable parameters, such as image noise thresholds, in the block 310 of FIG. 3. Other parameters may be employed in determining image quality goals, as described with reference to at least FIG. 3, and these may be pre-programmed into or preset in the system 100. Control then passes to a block 415.

In the block 415, comparison image quality parameters relevant to the conventional exposure strategies are determined. These image quality parameters may be computed from factors that are unique to the test subject 110 being examined, or may be extracted from a look-up table, or a combination of both may be employed as appropriate. Control then passes to a block 420.

In the block 420, a drive level to be modeled (as given by block 315 or block 350) is employed to determine image quality parameters appropriate to the kVp that is being modeled. In other words, expected image quality parameters for the selected trial voltage are computed in the block 420. As described above with reference to block 315 of FIG. 3, an initial test kVp setting is selected from a group of kVp settings that the system 100 is capable of. The initial selection is generally the lowest of the kVp settings that the system 100 offers. Control then passes to a block 425.

In the block 420, image quality parameters associated with conventional drive levels applied to the illumination source 104 that are suitable to the test subject 110 being imaged are determined. For example, a milli-Ampere level suitable for an X-ray illumination source 104 when a conventional kVp drive level is applied results in an expected image noise level. Control then passes to a block 425, whereby the process 400 ends and control passes back to the process 300 of FIG. 3.

Thus, in the block 325 of FIG. 3, a suitable current level to be applied to the illumination source 104 is computed when a drive level, such as the initial selected kVp setting, is determined that provides an image noise level that is consistent with an image noise level that would be achieved at a higher, conventional kVp drive level.

As shown in Table I supra, when the current level to the X-ray source is increased to maintain the same image noise level, the dose increases by 5% (at 120 kVp), 9% (at 100 kVp) and 24% (at 80 kVp), respectively, as compared to 140 kVp, thus providing the same visual image noise for the viewing windows as is expected by the radiologist using a conventional drive level applied to the illumination source 104, such as 140 kVp. The radiologist needs to clearly see the non-contrast-enhanced soft tissue in order to make a confident diagnosis, when a abnormality such, as a lesion is present, but preferably without increasing the dose of X-rays delivered to the patient (unless such is needed for reasons other than contrast, e.g., due to the patient's weight).

However, the equivalent dose kVp (ED) selection strategy described with reference to FIG. 4 permits effective imaging at reduced drive settings by selecting a current level that provides an illumination dose to the test subject 110 that is equivalent to that illumination dose delivered to the test subject 110 at a higher kVp setting and that provides an equivalent image quality goal as would have been achieved at the higher kVp setting. This is possible because the contrast improvements of soft tissue offer opportunity to increase the noise index by an amount that provides an equivalent dose (5% and 10% for 100 and 80 kVp).

The ED strategy of the process 400 increases the noise in the image over that to which the radiologist is accustomed, but still provides a soft tissue contrast to noise (CNR) advantage. That is, even though the image noise has increased, the contrast differences in HU values for soft tissue have increased by a greater amount. The CNR advantage with ED is reduced to 5% and 15% (100 kVp and 80 kVp, respectively) compared to the average values of 10% and 25% described above with reference to Table I.

Figure 5:
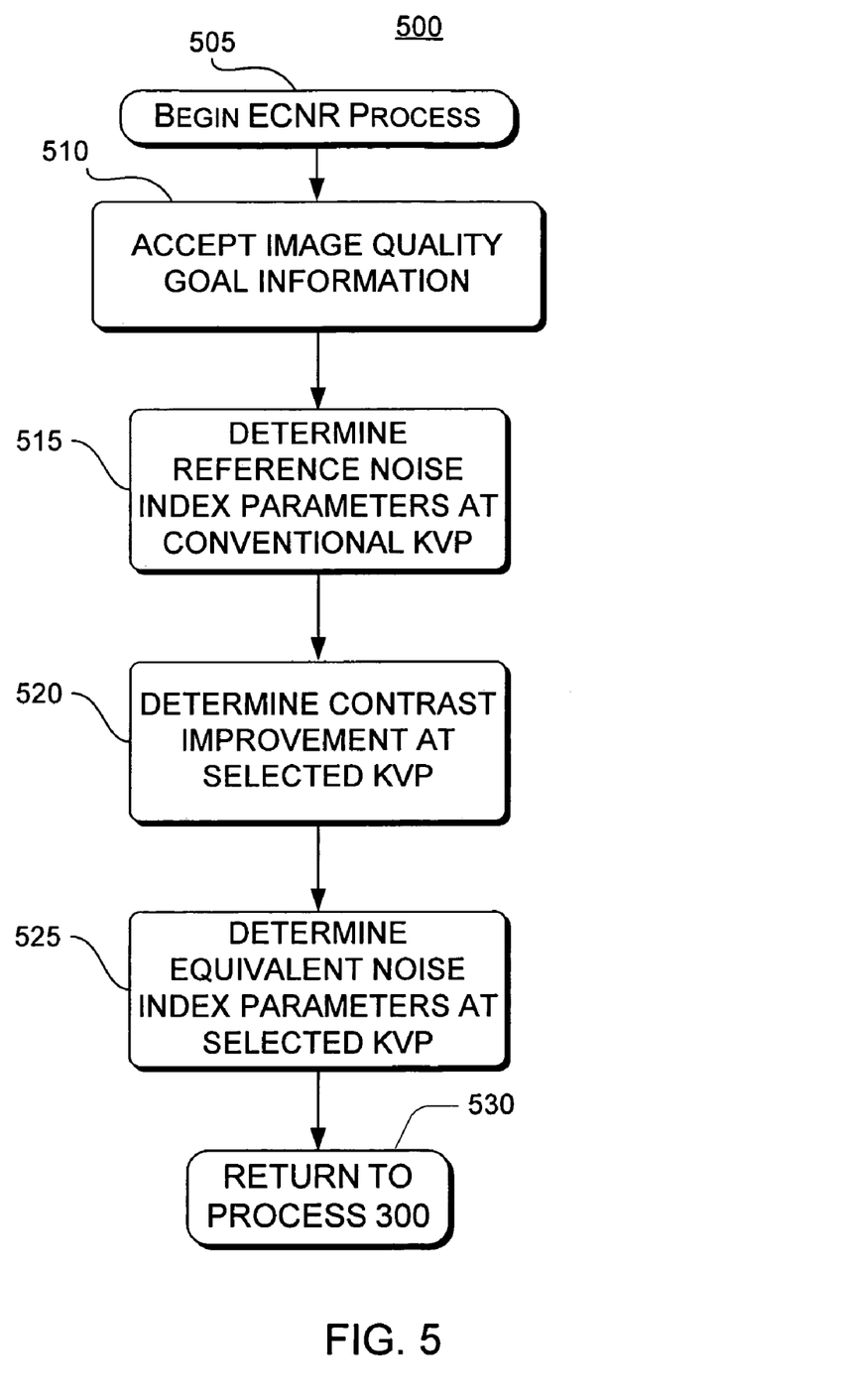
FIG. 5 shows a flowchart describing an Equivalent Noise to Contrast Ratio (ECNR) exposure process that finds utility in the system of FIG. 1.

FIG. 5 shows a flowchart describing an Equivalent Contrast to Noise Ratio (ECNR) exposure process 500 that finds utility in the system 100 of FIG. 1. The ECNR process 500 for reduced kVp selection is another strategy for selecting a kVp that is reduced in comparison to conventional exposure strategies, and proceeds by increasing the noise index to match the soft tissue contrast improvement. In turn, this provides a CNR equivalent to higher, conventional kVp selections (10% at 100 kVp and 25% and at 80 kVp). The ENCR process 500 begins in a block 505.

In a block 510, image quality goals selected by the radiologist in the block 310 of FIG. 3 are used to determine a reference noise index associated with conventional exposure strategies. Examples of various noise comparison indices are described above with respect to FIG. 3. Determination of reference noise indices may be a result of computations, based at least in part on aspects specific to the test subject 110, or may be taken from a lookup table, or may be an appropriate combination of computation and data stored in a lookup table. Control then passes to a block 515.

In the block 515, the reference noise index is employed to determine an equivalent noise index at the voltage that was selected in the block 315 or the block 350 of FIG. 3. The equivalent noise index may have a similar numerical value to that determined in the block 510, or may be scaled from that value by a predetermined amount, or may reflect noise index issues specific to the selected kVp, or may be a combination of these. Control then passes to a block 530, by which control is passed back to the process 300 of FIG. 3.

As a result, the ECNR process 500 increases image noise by the same or a similar or related factor as the soft tissue contrast increase. As shown in Table I supra, the noise index is increased by the same amount as the contrast ratio improvement results in dose reductions of 10% and 30% at 100 and 80 kVp, respectively, in this example.

Figure 6:
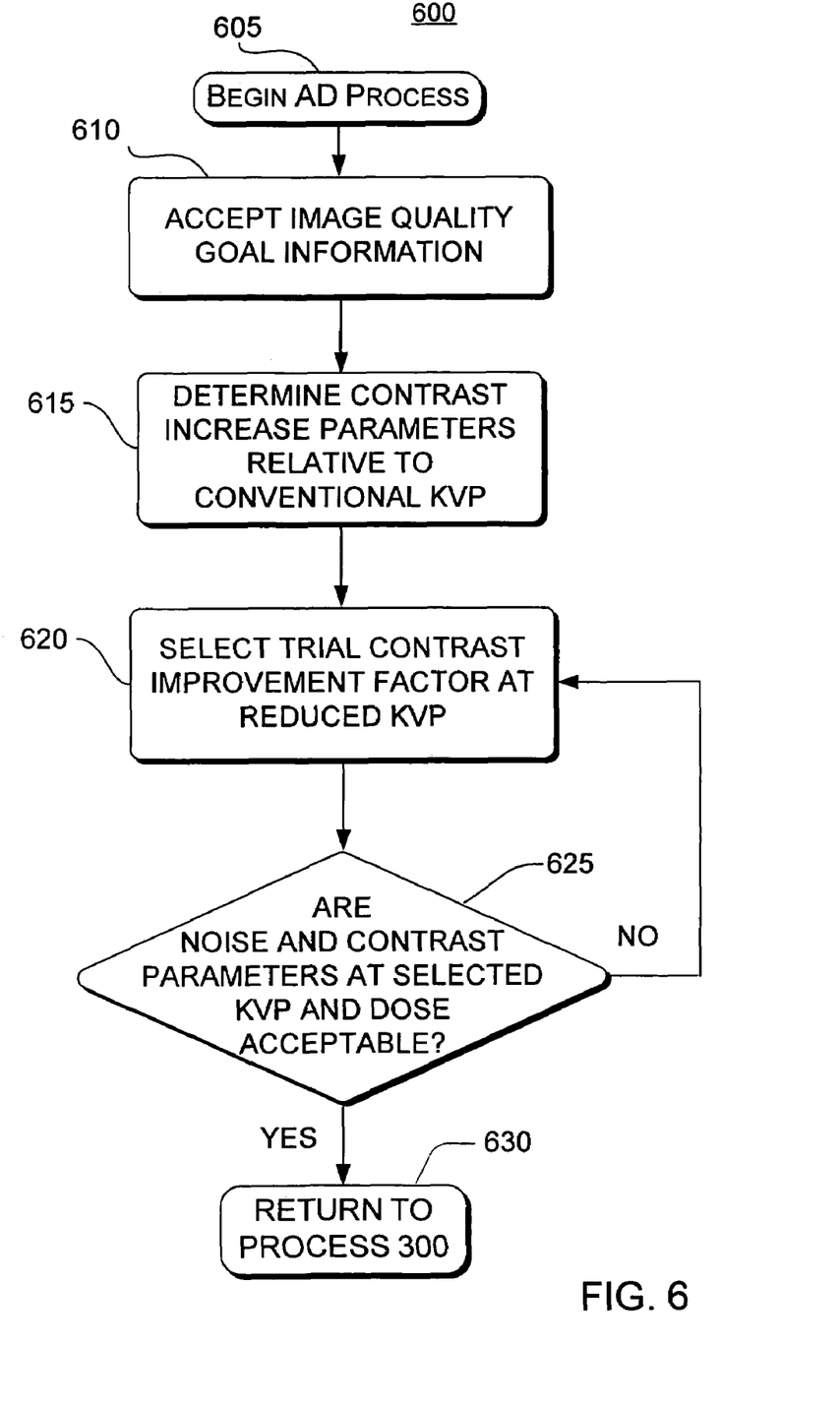
FIG. 6 shows a flowchart describing an Aggressive Dose Reduction (ADR) exposure process that finds utility in the system of FIG. 1.

FIG. 6 shows a flowchart describing an Aggressive Dose Reduction (ADR) exposure process 600 that finds utility in the system 100 of FIG. 1. The process 600 begins in a block 605.

In a block 610, the process 600 accepts image quality goal information, for example, user-specified image goal information as described above with reference to block 310 of FIG. 3. Control then passes to a block 615.

In the block 615, the process 600 determines contrast increase parameters that are possible in comparison to conventional imaging practices by employing a reduced kVp and/or employing a suitable contrast enhancement agent, as exemplified in Table I, supra. The possible contrast increase parameters for a given type of imaging task and imaging circumstances that are computed in the block 615 then may be used as "upper bounds" on contrast increase choices that may be considered in subsequent acts associated with the processes of the present disclosure. Control then passes to a block 620.

In the block 620, a trial contrast improvement factor, together with a corresponding a reduced kVp value and a reduced dosage of X-radiation delivered to the test subject 110, are selected for evaluation and are compared to conventional imaging parameters. Control then passes to a query task 625.

In the query task 625, expected noise and contrast parameters calculated for the selected kVp and dose values are evaluated to determine likelihood of acceptable or diagnostically relevant images. When the query task 625 determines that the expected noise and contrast parameters are not acceptable, control passes back to the block 620, and new trial contrast improvement parameters, together with concomitantly revised kVp and dose parameters are selected. When the query task 625 determines that the expected noise and contrast parameters appear to fall into an acceptable range, control passes to a block 630 to return to the process 300 of FIG. 3, and the process 600 terminates.

IV. Hardware and Operating Environment

Figure 7:
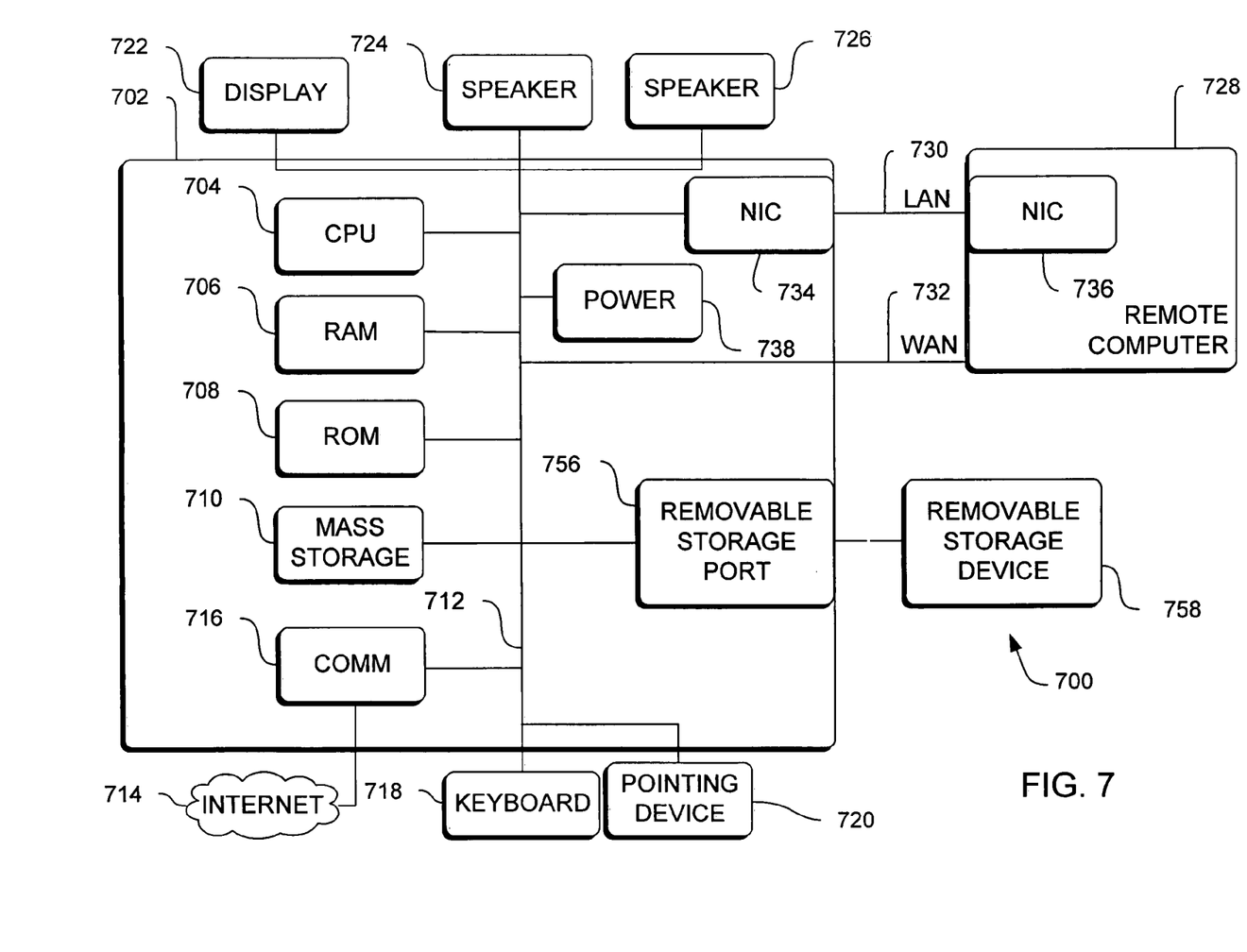
FIG. 7 is a block diagram of the hardware and operating environment in which different embodiments can be practiced.

FIG. 7 is a block diagram of a hardware and operating environment 700, including one or more computers 702, in which different embodiments can be practiced. The description of FIG. 7 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

The computer 702 includes one or more processors 704, commercially available from Intel, Motorola, Cyrix and others. The computer 702 also includes random-access memory (RAM) 706, read-only memory (ROM) 708, and one or more mass storage devices 710, and a system bus 712, that operatively couples various system components to the processing unit 704 and/or to each other and/or external apparatus. The memories 706 and 708, and the mass storage devices 710, are types of computer-accessible media. Mass storage devices 710 are more specifically types of nonvolatile computer-accessible media and can include one or more hard disk drives, floppy disk drives, optical disk drives, and tape cartridge drives. The processor 704 executes computer programs stored on these various computer-accessible media.

The computer 702 can be communicatively connected to the Internet 714 via a communication device 716. Internet 714 connectivity is well known within the art. In one embodiment, a communication device 716 is a modem that responds to communication drivers to connect to the Internet via what is known in the art as a "dial-up connection." In another embodiment, the communication device 716 includes an Ethernet® or similar hardware network card connected to a local-area network (LAN) that itself is connected to the Internet 714 via what is known in the art as a "direct connection" (e.g., T1 line, etc.).

A user enters commands and information into the computer 702 through input devices such as a keyboard 718 or a pointing device 720. The keyboard 718 permits entry of textual information into computer 702, as known within the art, and embodiments are not limited to any particular type of keyboard 718. The pointing device 720 permits the control of the screen pointer provided by a graphical user interface (GUI) of operating systems such as versions of the Microsoft Windows® operating system. Embodiments are not limited to any particular pointing or tactile input device 720. Such pointing devices 720 include mice, touch pads, trackballs, remote controls and point sticks. Other input devices (not shown) can include a microphone together with audio processing software, such as speech recognition software, joystick, game pad, satellite dish, scanner, or the like.

In some embodiments, the computer 702 is operatively coupled to a display device 722 via the system bus 712. The display device 722 permits the display of information, including computer, video and other information, for viewing by a user of the computer 702. Embodiments are not limited to any particular display device 722, which may include cathode ray tube (CRT) displays (monitors), as well as flat panel displays such as liquid crystal displays (LCD's). In addition to a monitor 722, computers 702 typically include other peripheral input/output devices such as printers (not shown). Speakers 724 and 726 may provide audio output signals, responsive to commands delivered through the system bus 712.

The computer 702 also includes an operating system (not shown) that is stored on the computer-accessible media RAM 706, ROM 708, and mass storage device 710, that is accessed and executed by the processor 704. Examples of operating systems include the Microsoft Windows®, Apple MacOS®, Linux® and UNIX® operating systems. Examples are not limited to any particular operating system, however, and the construction and use of such operating systems are well known within the art.

Embodiments of the computer 702 are not limited to any type of computer 702. In varying embodiments, the computer 702 comprises a PC-compatible computer, a MacOS® operating system compatible computer, a Linux® operating system compatible computer, or a UNIX® operating system compatible computer. The construction and operation of such computers are well known within the art.

The computer 702 can be operated using at least one operating system to provide a graphical user interface (GUI) including a user-controllable pointer. The computer 702 can have at least one web browser application program executing within at least one operating system, to permit users of the computer 702 to access an intranet, extranet or Internet 714 world-wide-web pages as addressed by Universal Resource Locator (URL) addresses. Examples include the Netscape Navigator® and the Microsoft Internet Explorer® browser programs.

The computer 702 can operate in a networked environment using logical connections to one or more remote computers, such as a remote computer 728. These logical connections are achieved by a communication device coupled to, or forming a part of, the computer 702. Embodiments are not limited to a particular type of communications device. The remote computer 728 can be another computer, a server, a router, a network PC, a client, a peer device or other common network node. The logical connections depicted in FIG. 7 include a local-area network (LAN) 730 and a wide-area network (WAN) 732. Such networking environments are commonplace in offices, enterprise-wide computer networks, intranets, extranets and the Internet 714.

When used in a LAN-networking environment, the computer 702 and remote computer 728 are connected to the local network 730 through network interfaces or adapters 734, which is one type of communications device 716. The remote computer 728 also includes a network device 736. When used in a conventional WAN-networking environment, the computer 702 and remote computer 728 communicate with a WAN 732 through one or more modems (not shown). The modem, which can be internal or external, is connected to the system bus 712. In a networked environment, program modules depicted relative to the computer 702, or portions thereof, can be stored in the remote computer 728.

The computer 702 also includes a power supply 738. Each power supply 738 can be a battery. The computer 702 also may include a removable memory storage port 756 capable of accepting a removable data storage device 758 (analogous to the port 156 and removable data storage device 158 of FIG. 1). Computer-readable instructions and/or data may be supplied to the computer 720 via coupling to a suitably-programmed removable data storage device 758 and/or via a carrier wave including modulation of computer-readable information coupled from external sources, such as the Internet 714 or other external interconnections.

The computer 702 may function as one or more of the control segments of module 120 (FIG. 1), the computer 130, the operator console 140 and/or the data acquisition and conditioning module 160, for example, via implementation of the processes 300, 400, 500 and 600 of FIGS. 3 through 6 as computer program modules.

V. Conclusion

A computer-based medical imaging system is described. Although specific embodiments have been illustrated and described herein, it will be appreciated by those of ordinary skill in the art that any arrangement which is calculated to achieve the same purpose may be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this disclosure is meant to include all object-oriented, database and communication environments and alternate technologies which provide the same functionality as described herein.

What is claimed is:

1. A process for managing dose and contrast in a non-destructive imaging system, comprising:
accepting user input data indicative of image quality goals and a drive parameter setting strategy for an illumination source to be employed in the non-destructive imaging of an internal portion of a test subject;
determining when the non-destructive imaging system is capable of achieving the image quality goals using a particular drive parameter setting selected from among a group of achievable drive parameter settings, a first of the group of drive parameter settings corresponding to a lowest drive parameter setting for the non-destructive imaging system, the first drive parameter setting being initially chosen as the particular drive parameter setting;
proceeding with a non-destructive imaging procedure when the act of determining does not indicate that the non-destructive imaging system is incapable of achieving the image quality goals at the particular drive parameter setting;
replacing the particular drive parameter setting with an incrementally increased particular drive parameter setting when the act of determining indicates that the non-destructive imaging system is not capable of achieving the image quality goals at the particular drive parameter setting; and
iterating the acts of determining, proceeding or increasing and iterating, until either proceeding is achieved or all available drive parameter settings have been tested, and, including an act of generating a message to an operator of the system when all drive parameter settings have been tested and the act of determining continues to indicate incapability.

2. The process of claim 1, wherein the act of accepting comprises an act of accepting a user input selection among: an equivalent dose strategy; an equivalent contrast to noise ratio strategy; and an aggressive dose reduction strategy.

3. The process of claim 1, wherein the act of proceeding with a non-destructive imaging procedure includes an act of proceeding with an X-ray imaging procedure, and wherein the test subject is a living patient.

4. The process of claim 1, wherein the act of proceeding with a non-destructive imaging procedure includes an act of proceeding with an X-ray imaging procedure, and further comprising, after proceeding, an act of obtaining image data relative to at least some internal portion of the test subject, and further comprising an act of remapping the image data from Hounsfield Units to Hounsfield Normalized Units, where a slope of Hounsfield Normalized Units maintains contrast over an interval corresponding to a selected imaging task.

5. The process of claim 1, wherein the act of proceeding with a non-destructive imaging procedure includes an act of proceeding with an X-ray imaging procedure, and wherein the group of achievable drive parameter settings includes voltages to be applied to an X-ray illumination source, the voltages ranging from at least 80 kiloVolts peak to at least 140 kiloVolts peak.

6. The process of claim 1, wherein the act of proceeding with a non-destructive imaging procedure includes an act of proceeding with an X-ray imaging procedure, and wherein the lowest drive parameter setting includes a voltage of 80 kiloVolts peak or less to be applied to an X-ray illumination source, and wherein the act of replacing the particular drive parameter setting with an incrementally increased particular drive parameter setting comprises an act of increasing the voltage in 20 kiloVolt increments.

7. The process of claim 1, further including an act of an act of generating a message to an operator of the system to reduce a scan speed of an X-ray imaging system when the acts of iterating and determining continue to indicate incapability.

8. A non-destructive imaging system, comprising:
an illumination source configured to internally illuminate a test subject in generating an image of at least an internal portion of a test subject;
a controllable driver coupled to the illumination source, the controllable driver including capability for multiple drive parameter settings for the illumination source;
a user interface capable of accepting user input data indicative of image quality goals and a user choice of at least one of a plurality of drive parameter selection strategies for the illumination source; and
a control module configured to:
initially select a lowest of the multiple drive parameter settings as a selected setting;
model the selected setting in the context of the user choice of drive parameter selection strategies to determine when the selected setting is capable of achieving the image quality goals, and;
when a the control module test indicates that the image quality goals cannot be met at the selected setting, replacing the selected setting with an incrementally increased value for the selected setting and repeating the control module test; and
when the control module test indicates that the image quality goals can be met at the selected setting, proceeding with imaging the test subject.

9. The system of claim 8, wherein the illumination source comprises an X-ray illumination source capable of accepting peak voltages in a range extending from at least 80 kVp to 140 kVp.

10. The system of claim 8, wherein the illumination source comprises an X-ray illumination source capable of accepting peak voltages in a range extending at least below 100 kVp.

11. The system of claim 8, wherein the illumination source comprises an X-ray illumination source capable of accepting peak voltages in a range extending at least below 100 kVp, and the user interface includes capability for accepting user input data indicative of a user choice of at least one of: conventional imaging parameters; an automatic exposure control strategy; an equivalent dose imaging strategy; an equivalent noise to contrast ratio strategy; and an aggressive dose reduction strategy.

12. The system of claim 8, wherein the illumination source includes an X-ray illumination source, and the user interface includes capability for accepting user input data indicative of a user choice of at least one of: conventional imaging parameters; an automatic exposure control strategy;

an equivalent dose imaging strategy; an equivalent noise to contrast ratio strategy; and an aggressive dose reduction strategy.

13. The system of claim 8, wherein the illumination source includes an X-ray illumination source capable of low voltage operation, and wherein the system further includes a data acquisition and conditioning module configured to adjust a window for display of imaging data from the system in response to user input, and to permit selection between at least: a conventional Hounsfield Unit scale; a piece-wise linear Hounsfield Normalized scale; and a modified-slope Hounsfield Normalized scale, for data representation.

14. The system of claim 8, wherein the illumination source includes an X-ray illumination source and the system further includes a data acquisition and conditioning module configured for remapping image data from Hounsfield Units to Hounsfield Normalized Units, where a slope of Hounsfield Normalized Units increases contrast over an interval corresponding to a selected imaging task and renders information falling outside of the interval to an extremal value.

15. The system of claim 8, wherein the illumination source comprises an X-ray illumination source capable of accepting peak voltages in a range including a range extending from below at least 100 kVp up to at least 120 kVp, and wherein the control module is further configured to display, to an operator of the system, information including selected settings for contrast, image noise and drive parameters to be applied to the illumination source.

16. The system of claim 8, wherein:
the illumination source comprises an X-ray illumination source capable of accepting peak voltages in a range extending at least below 100 kVp;
the user interface includes capability for accepting user input data indicative of a user choice of at least one of: conventional imaging parameters; an automatic exposure control strategy; an equivalent dose imaging strategy; an equivalent contrast to noise ratio strategy; and an aggressive dose reduction strategy; and
the system further includes a data acquisition and conditioning module configured to adjust a window for display of imaging data from the system in response to user input, and to permit selection between at least: a conventional Hounsfield Unit scale; a piece-wise linear Hounsfield Normalized scale; and a modified-slope Hounsfield Normalized scale, for data representation.

17. A computer-readable medium having computer code embodied thereon that includes computer-readable instructions, which, when executed by one or more processors, causes the one or more processors to perform acts of:
accepting user input data indicative of image quality goals and a drive parameter setting strategy for a high-power X-ray source to be employed in non-destructive imaging of a test subject using an X-ray system;
determining when the X-ray system is capable of achieving the image quality goals using a particular drive parameter setting selected from among a group of achievable drive parameter settings, a first of the group of drive parameter settings corresponding to a lowest drive parameter setting for the high-power X-ray source, the first drive parameter setting being initially chosen as the particular drive parameter setting;
proceeding with an X-ray procedure when determining does not indicate that the X-ray system is incapable of achieving the image quality goals at the particular drive parameter setting;
replacing the particular drive parameter setting with an incrementally increased particular drive parameter setting when determining indicates that the X-ray system is not capable of achieving the image quality goals; and
iterating determining, proceeding or increasing and iterating, until either proceeding is achieved or all available drive parameter settings have been tested, and, when all drive parameter settings have been tested and determining continues to indicate incapability, generating an error message.

18. The computer-readable medium of claim 17, wherein the high-power X-ray source includes an X-ray source capable of low voltage operation, and wherein the computer-readable code is further configured to cause the one or more processors to perform acts of:
adjusting a window for displaying imaging data from the system in response to user input; and
permitting selection between at least: a conventional Hounsfield Unit scale; a piece-wise linear Hounsfield Normalized scale; and a modified-slope Hounsfield Normalized scale, for data representation.

19. The computer-readble medium of claim 17, wherein the high-power X-ray source includes an X-ray source capable of multiple voltages for operation, and wherein the computer-readable code is further configured to cause the one or more processors to perform acts of:
accepting a user input selection indicative of multiple X-ray exposure strategies; and
testing the user input selection to determine effective dose reduction and image quality parameters consistent with rendering a diagnostically useful image of a test subject.

20. The computer-readable medium of claim 17, wherein the high-power X-ray source includes an X-ray source capable of multiple voltages for operation, the voltages extending to a lower limit of at least 80 kVp, and wherein the computer-readable code is further configured to cause the one or more processors to perform acts of:
accepting a user input selection indicative of multiple X-ray exposure strategies chosen from among at least: conventional imaging parameters; an automatic exposure control strategy; an equivalent dose imaging strategy; an equivalent noise to contrast ratio strategy; and an aggressive dose reduction strategy; and
testing the user input selection to determine effective dose reduction and image quality parameters consistent with rendering a diagnostically useful image of a test subject.

* * * * *